(12) United States Patent
Fuller et al.

(10) Patent No.: US 8,046,072 B2
(45) Date of Patent: Oct. 25, 2011

(54) PRIORITIZATION OF COMMUNICATIONS FROM MEDICAL DEVICES

(75) Inventors: Chris C. Fuller, Bloomington, MN (US); Javaid Masoud, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 551 days.

(21) Appl. No.: 11/095,396

(22) Filed: Mar. 31, 2005

(65) Prior Publication Data

US 2006/0224213 A1  Oct. 5, 2006

(51) Int. Cl.
*A61N 1/37* (2006.01)
*G08B 23/00* (2006.01)
*G08B 1/08* (2006.01)

(52) U.S. Cl. ........ 607/32; 607/60; 340/539.12; 340/517

(58) Field of Classification Search .............. 607/32, 607/60; 128/903, 904; 340/517, 519, 539.12, 340/506, 573.1
See application file for complete search history.

(56) References Cited

U.S. PATENT DOCUMENTS

| | | | |
|---|---|---|---|
| 5,749,045 A | 5/1998 | Benz et al. | |
| 6,213,942 B1 | 4/2001 | Flach et al. | |
| 6,259,355 B1 * | 7/2001 | Chaco et al. | 340/286.07 |
| 6,441,747 B1 | 8/2002 | Khair et al. | |
| 6,589,169 B1 * | 7/2003 | Surwit et al. | 600/300 |
| 6,763,269 B2 | 7/2004 | Cox | |
| 2002/0115916 A1 | 8/2002 | Sjoqvist | |
| 2003/0220673 A1 | 11/2003 | Snell | |
| 2004/0081135 A1 | 4/2004 | Ewing et al. | |
| 2004/0122297 A1 | 6/2004 | Stahman et al. | |
| 2004/0215270 A1 * | 10/2004 | Ritscher et al. | 607/27 |
| 2005/0060186 A1 | 3/2005 | Blowers et al. | |

FOREIGN PATENT DOCUMENTS

EP  1495783 A1  12/2005

OTHER PUBLICATIONS

International Search Report for PCT/US2006/010593.
Written Opinion of the International Searching Authority for PCT/US2006/010593.

* cited by examiner

*Primary Examiner* — Carl H. Layno
*Assistant Examiner* — Tammie K Heller

(57) ABSTRACT

Device data is generated at each medical device in a system including a plurality of medical devices. Priority information is dynamically assigned to the device data at each medical device based on the character of the device data. The device data and the priority information are transmitted from each medical device. Interfering communications of device data and priority information from multiple medical devices are processed successively based on the priority information.

14 Claims, 2 Drawing Sheets

US 8,046,072 B2

PRIORITIZATION OF COMMUNICATIONS FROM MEDICAL DEVICES

BACKGROUND OF THE INVENTION

The present invention relates to communicating data between medical devices and a processing unit. More specifically, the present invention relates to prioritizing and trafficking simultaneous interfering telemetric communications by multiple medical devices with a processing unit.

There have been considerable advancements in both the field of electronics and medicine, such that there is presently a wide assortment of commercially available body-implantable and non-implantable electronic medical devices. The class of medical devices now includes pacemakers, implantable cardioverter defibrillators, neural stimulators, and drug administering devices, among others. Today's state of the art medical devices are vastly more sophisticated and complex than early ones, and are capable of performing significantly more complex tasks. The therapeutic benefits of these devices have been well proven.

It has proven useful for medical devices to have the capability of communicating data wirelessly with a processing unit that in turn is capable to process, store, and/or display data provided by the medical device. The data provided by the medical device may be real-time or recorded data. The processing unit may also transmit signals to the medical device in order to provide some control over the medical device. This communication is achieved by wireless telemetry, which involves wireless data transfer between the medical device and the processing unit or another medical device using radio frequency (RF) signals, infrared (IR) frequency signals, or other electromagnetic signals.

At present, a medical device attempting to communicate information may open a communication session ad hoc. As medical devices become more prevalent, the possibility increases that multiple medical devices (either in the same patient or in different patients) will attempt to communicate simultaneously. Various communications technologies currently exist that allow multiple communications to be processed simultaneously. For example, communications in time division multiple access (TDMA) systems are assigned blocks of time in which to transmit data, communications in frequency division multiple access (FDMA) systems are assigned channels within a frequency in which to transmit data, and communications in Quad-QAM modulated systems employ aspects of both TDMA and FDMA systems. However, since the frequencies available for telemetric communication by medical devices are limited, the potential for simultaneous communications from multiple medical devices attempting to communicate during the same block of time or on the same channel also increases. This may cause errors in communications between a medical device and another medical device or a processing unit. For example, one medical device may be prevented from communicating if the channel is occupied by another medical device, which is also communicating. In addition, the communications between one medical device and the processing unit may be interrupted by another medical device attempting to communicate with the processing unit. This is especially troublesome if an urgent communication to or from a medical device is prevented or interrupted by another medical device try to access the same transceiver or similar host.

BRIEF SUMMARY OF THE INVENTION

The present invention is a system and method for prioritizing interfering communications from a plurality of medical devices. Device data is generated at each medical device, and priority information is dynamically assigned to the device data at each medical device based on the character of the device data. The device data and the priority information are transmitted from each medical device. Interfering communications of device data from the plurality of medical devices are successively based on the priority information assigned to the device data.

DETAILED DESCRIPTION

Figure 1:
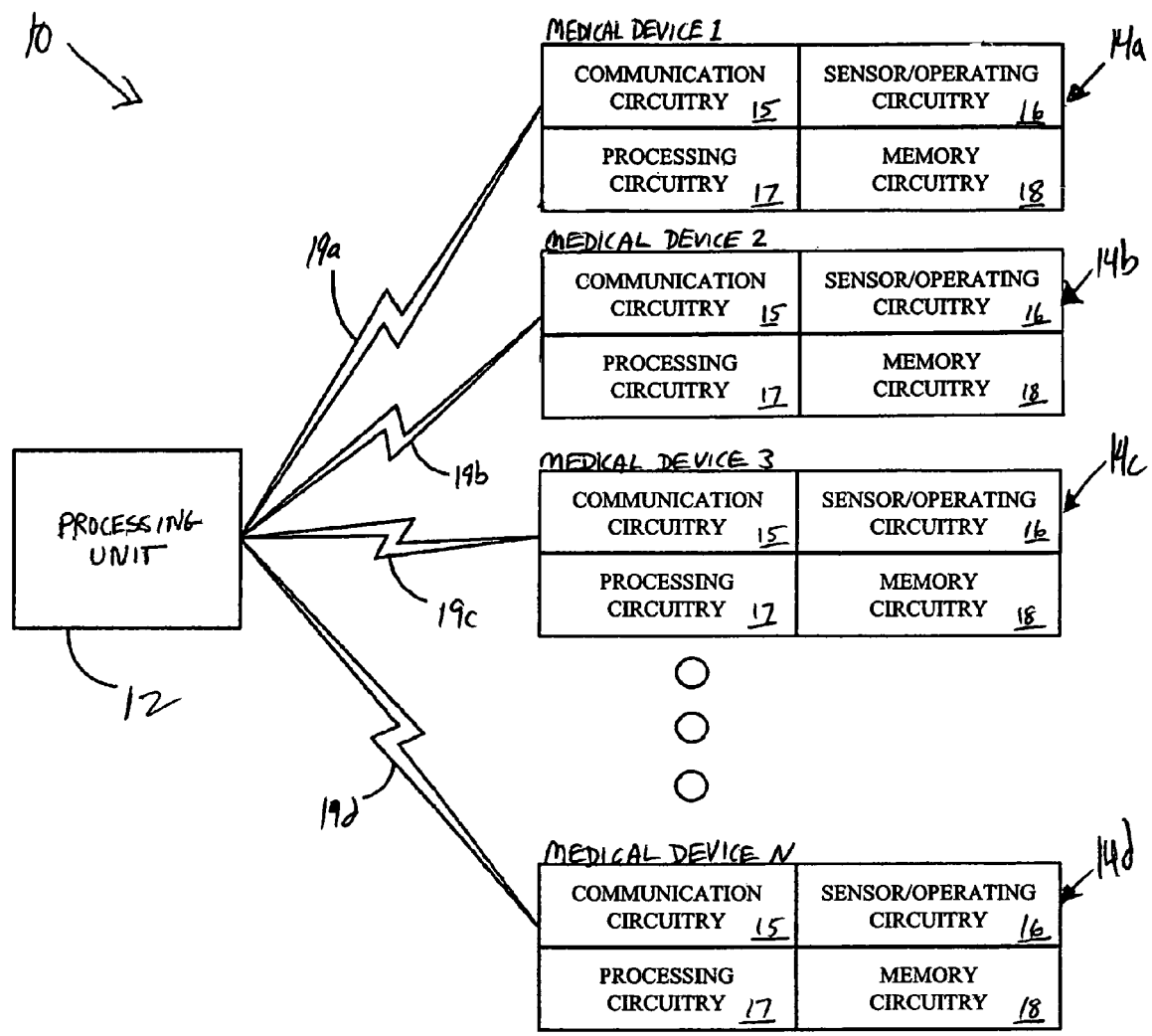
FIG. 1 is a block diagram of a system illustrating telemetry between a processing unit and a plurality of medical devices.

FIG. 1 is a block diagram of system 10 illustrating telemetry between processing unit 12 and a plurality of medical devices 14a, 14b, 14c, and 14d. Each medical device 14a-14d includes communication circuitry 15, sensor/operating circuitry 16, processing circuitry 17, and memory circuitry 18. Medical devices 14a-14d each represent one of a variety of medical devices that are operable to communicate with processing unit 12 telemetrically, and may be either different devices implanted in or employed by different patients, or different devices implanted in or employed by the same patient. Medical devices 14a-14d may represent an implantable medical device (IMD), such as an implantable cardiac pacemaker, an implantable defibrillator, an implantable pacemaker/cardioverter/defibrillator, an implantable muscular stimulus device, an implantable brain stimulator, an implantable nerve stimulator, an implantable drug delivery device, an implantable monitor, or the like. In addition, medical devices 14a-14d as described with regard to the present invention may be non-implantable devices capable of communicating telemetrically.

Processing unit 12 may be embodied in a variety of configurations. For example, processing unit 12 may be an external computer system at a clinician's office (e.g., a programmer). Alternatively, processing unit 12 may be embodied in an identification card, a pendant, a laptop computer, a hand-held computer, a pager, or the like. In addition, processing unit 12 may comprise a device worn on a patient's wrist, around a patient's neck, around a patient's waist, on a patient's skin (i.e., as an adhesive patch), and so on. Furthermore, processing unit 12 may comprise a programmed computer used by emergency medical personnel (e.g., in an ambulance) to communicate with a variety of possible medical devices that may be implanted within a given patient. These and other configurations for processing unit 12 may be used in accordance with the present invention.

Processing unit 12 communicates with medical devices 14a, 14b, 14c, and 14d (in particular, communication circuitry 15) via telemetry signals 19a, 19b, 19c, and 19d, respectively. Telemetry signals 19a-19d may be radio frequency (RF) signals, infrared (IR) signals, or other electromagnetic signals. In addition, telemetry signals 19a-19d may be non-electromagnetic signals, such as acoustical signals. Telemetry signals 19a-19d may also be based on high frequency wireless communication protocols, such as cellular telephony, wireless PBX, Bluetooth, ZigBee, and the like. Processing unit 12 may use telemetry signals 19a-19d, for example, to program medical devices 14a-14d, respectively, to control operation of sensor/operating circuitry 16 for delivering a particular therapy to a patient, such as electrical stimulation, drug administration, or the like. In addition, medical devices 14a-14d may use telemetry signals 19a-19d, respectively, to send information to processing unit 12 relating to the operation of sensor/operating circuitry 16, such as diagnostic information, sensed conditions associated with the patient, or any other information collected or identified by the medical device.

In one example of a communication session between processing unit 12 and one of medical devices 14a-14d, a telemetry session is initiated by "waking up" the medical device with a magnet, a wireless transmission to communication circuitry 15, or other initiating means. This is done, for example, to deliver a particular therapy to the patient, download medical data from the device, or determine the status of the device. Alternatively, one of medical devices 14a-14d may initiate a telemetry session by transmitting (via communication circuitry 15) an initiating sequence to processing unit 12 or by other initiating means. This may occur, for example, if the medical device is only capable of transmitting information (i.e., cannot receive information) or if an urgent medical situation arises in the patient or if the device battery is low. In either case, the medical device subsequently transmits device identification information, and processing unit 12 then identifies the medical device and loads or executes an appropriate application program. Processing unit 12 may then interrogate the medical device to determine the configuration of the device and to retrieve data stored in the medical device. Alternatively, if it is only capable of transmitting information, the medical device transmits configuration information and data stored in the medical device without interrogation. The retrieved data is then manipulated by the application program to generate an output from processing unit 12 (e.g., a warning displayed to the clinician, a change in therapy to be administered by the medical device, the raw device data provided in an analyzable format, etc.).

As discussed previously, as implantable and non-implantable medical devices with telemetry capability become more prevalent, the possibility of multiple medical devices 14a-14d desiring to communicate simultaneously increases. Various communications technologies currently exist that allow simultaneous communications to share frequencies or blocks of time (e.g., time division multiple access, frequency division multiple access, etc.). However, since the frequencies available for telemetric communication are limited, the potential for simultaneous communications from medical devices 14a-14d interfering with each other also increases.

Figure 2:
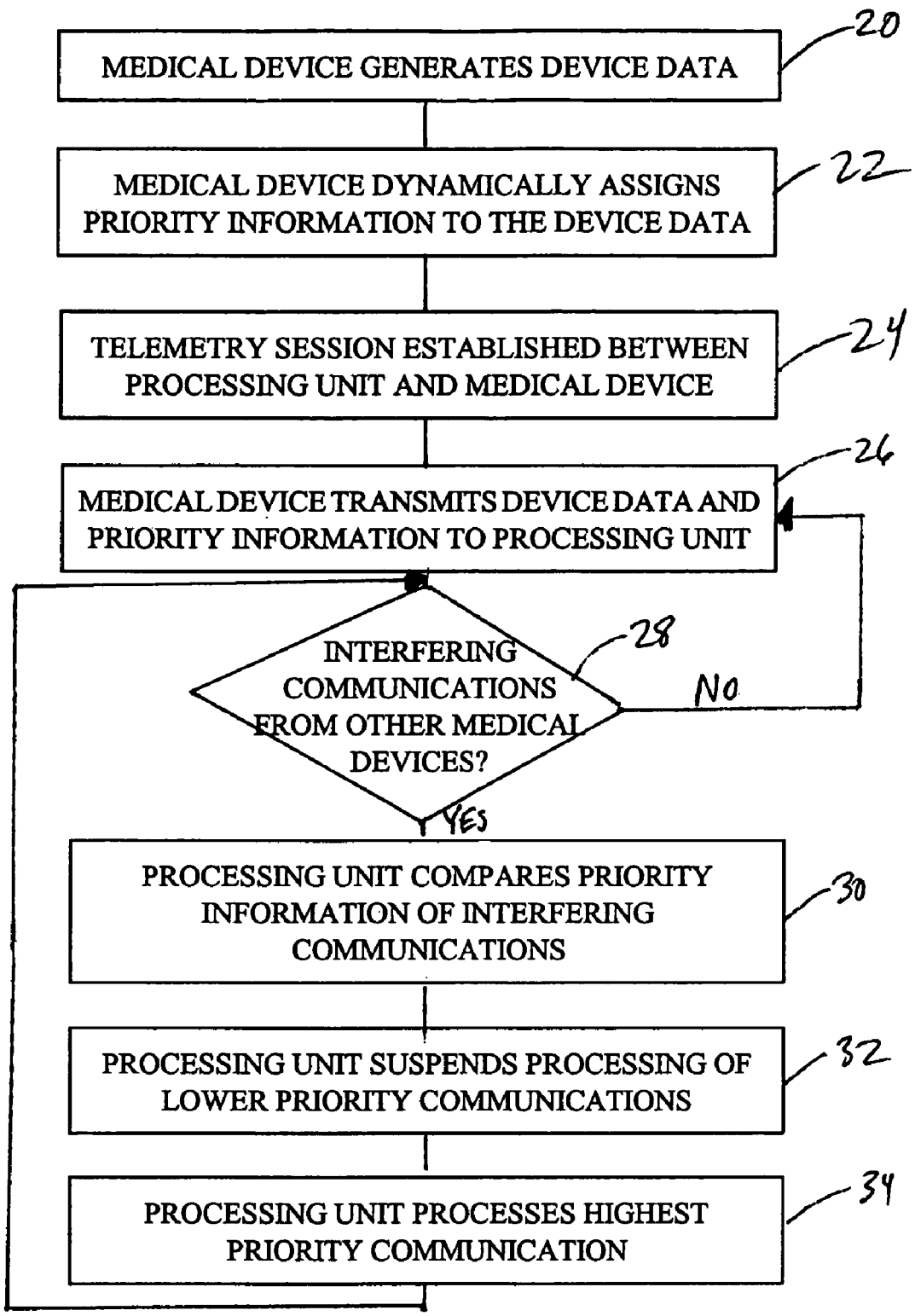
FIG. 2 is a flow diagram illustrating the process by which a processing unit prioritizes interfering communications from multiple medical devices according to an embodiment of the present invention.

FIG. 2 is a flow diagram illustrating the process by which processing unit 12 prioritizes interfering communications from multiple medical devices 14a-14d according to an embodiment of the present invention. When implanted or used in a patient, each medical device 14a-14d provides therapy and/or generates device data (block 20). This operation is performed by sensor/operating circuitry 16. The device data generated may be any information related to the operation of medical devices 14a-14d that a clinician or technician may find useful, such as medical data and device status data.

As the device data is generated by medical devices 14a-14d, each medical device 14a-14d dynamically assigns priority information to the device data (block 22). Processing circuitry 17 processes the device data and assigns priority information to the device data based on the character of the device data. For example, the priority information may be assigned based on the urgency of the device data generated. In the case of a medical situation, the level of urgency of the device data may be set by applying a triaging algorithm to the data. In the case of other types of device data, the level of urgency of the device data may be determined based on the immediate need for attention to the data. As another example, the priority information may be assigned based on a preset priority classification structure stored in each medical device 14a-14d or assigned by processing unit 12. For instance, data produced by a medical device that is only capable of transmitting information may be assigned priority information by processing unit 12 or based on preprogrammed information in the medical device. In any case, because the priority information is dynamically assigned for each medical device 14a-14d, the priority information remains current with respect to the device data generated at all times. The device data and assigned priority information is stored in memory circuitry 18.

To communicate information between processing unit 12 and medical devices 14a-14d, a telemetry session may be established between processing unit 12 and medical devices 14a-14d (block 24). A telemetry session may be initiated as described above by either processing unit 12 or one of the medical devices. Once a telemetry session has been established, the medical device involved in the telemetry session (e.g., device 14c) transmits its device data and the priority information assigned to the device data to processing unit 12 (block 26). In one embodiment, the device data and the priority information are transmitted in a single communication frame. The priority information includes an identification portion to associate the priority information with the device data to which it relates.

As processing unit 12 and device 14c communicate, processing unit 12 monitors the communication medium to assure that no other medical devices are attempting to establish an interfering telemetry session (e.g., on the same frequency as is being used for the established telemetry session), as indicated by block 28. While none of the other medical devices 14a, 14b, and 14d are attempting to communicate, device 14c in the established telemetry session continues to transmit device data and dynamically updated priority information to processing unit 12.

If one of the other medical devices (e.g., device 14a) attempts to establish an interfering telemetry session, processing unit 12 compares the priority information associated with the device data in the established telemetry session with the priority information associated with the interfering communications, as indicated by block 30. Processing unit 12 then temporarily suspends processing of communications of device data having lower assigned priority information (block 32) and processes the device data having the highest assigned priority information (block 34). Thus, processing of device data in an established telemetry session may be temporarily suspended in favor of establishing a telemetry session with a medical device having device data with higher associated priority information. This allows any medical device 14a-14d to immediately establish a telemetry session with processing unit 12 if it has urgent or other high priority data to communicate to processing unit 12. While processing the device data having the highest priority level, processing unit 12 determines whether other medical devices have attempted or are attempting to establish an interfering telemetry session, as indicated by the return to block 28. After processing unit 12 finishes processing the highest priority communication, processing unit 12 subsequently processes the device data having the next highest priority information (which becomes the device data with the new highest priority information). It should be noted that in the instance that two or more medical devices 14a-14d having identical priority information attempt to communicate at the same time, processing unit 12 may process the communications based on the order of receipt of the communications, or at the same time using known communication technologies (e.g., TDMA, FDMA, etc.).

Accordingly, as implantable medical devices with telemetry capabilities become more prevalent, the possibility of multiple implantable medical devices attempting to communicate simultaneously with an external unit or each other increases. Due to limited available frequencies, the potential for simultaneous communications from multiple implantable medical devices interfering with each other also increases, which may cause communications errors. The present invention is a system and method for prioritizing interfering communications from a plurality of implantable medical devices. Device data is generated at each medical device, and priority information is dynamically assigned to the device data at each medical device based on a character of the device data. The device data and the priority information are transmitted from each medical device. Interfering communications of device data from the plurality of implantable medical devices are processed successively based on the priority information assigned to the device data.

Although the present invention has been described with reference to preferred embodiments, workers skilled in the art will recognize that changes may be made in form and detail without departing from the spirit and scope of the invention. For example, while the embodiments shown are directed to prioritizing simultaneous interfering communications from multiple medical devices 14a-14d, the present invention is applicable in a system including multiple processing units 12 that attempt to interferingly communicate. That is, priority information may be dynamically assigned to all communications in a system including multiple processing units 12 as well as multiple medical devices 14a-14d.

The invention claimed is:

1. A method for prioritizing communications from a plurality of implanted medical devices to a processing unit, at least two of the plurality of implanted medical devices being subcutaneously implanted in different patients, the method comprising:
   automatically generating device data from subcutaneously implanted sensors at each implanted medical device;
   dynamically assigning priority information to the device data at each implanted medical device based on a character of the device data; then
   communicating the device data and the priority information from each implanted medical device to the processing unit; and
   processing, with the processing unit, simultaneous interfering communications of device data and priority information from the plurality of implanted medical devices based on the priority information.

2. The method of claim 1, wherein dynamically assigning priority information to the device data at each implanted medical device based on a character of the device data comprises:
   dynamically assigning priority information to the device data based on an urgency of the device data generated.

3. The method of claim 1, wherein communicating the device data and the priority information from each implanted medical device comprises:
   interrogating each implanted medical device for the device data; and
   transmitting the device data and the priority information.

4. The method of claim 3, wherein the device data and the priority information are transmitted in a common communication platform.

5. The method of claim 1, wherein processing simultaneous interfering communications of device data and priority information from the plurality of implanted medical devices based on the priority information comprises:
   temporarily suspending processing of lower priority interfering communications; and
   processing a highest priority interfering communication.

6. The method of claim 5, wherein processing simultaneous interfering communications of device data and priority information from the plurality of implanted medical devices based on the priority information further comprises:
   processing a next highest priority interfering communication subsequent to processing of the highest priority interfering communication.

7. In a system comprising a plurality of implanted medical devices and a processing unit, wherein a first of the plurality of implanted medical devices is subcutaneously implanted in a first patient and a second of the plurality of implanted medical devices is subcutaneously implanted in either the first patient or a second patient, and wherein each of the plurality of implanted medical devices is operable to communicate device data, wherein each implanted medical device generates the device data and dynamically assigns a priority level to the device data based on a classification of the device data, a method of coordinating interfering communications of device data between multiple implanted medical devices, the method comprising:
   comparing the relative priority levels assigned to the device data in each of the interfering communications with the processing unit; and
   processing each of the interfering communications with the processing unit based on the respective priority levels assigned to the device data in each of the interfering communications.

8. The method of claim 7, wherein processing each of the interfering communications in an order based on the respective priority levels assigned to the device data in each of the interfering communications comprises:
   temporarily suspending processing of interfering communications with lower priority levels; and
   processing an interfering communication with a highest priority level.

9. The method of claim 8, wherein processing each of the interfering communications in an order based on the respective priority levels assigned to the device data in each of the interfering communications further comprises:
   processing an interfering communication with a next highest priority level subsequent to processing the interfering communication with the highest priority level.

10. The method of claim 7, wherein the classification of the device data is based on an urgency of the device data being transmitted.

11. The method of claim 7, wherein the classification of the device data is based on a priority classification structure stored in the implanted medical device.

12. A system comprising:
   a plurality of medical devices a first one of which is configured to be implanted in a first patient and a second one of which is configured to be implanted in a second patient different from the first patient, each of the plurality of medical devices having implanted sensors and being operable to automatically generate and transmit device data and priority information about the device data, the priority information being dynamically updated at each medical device based on a character of the device data being transmitted; and a processing unit operable to receive the device data and priority information, wherein the processing unit processes interfering transmissions from the plurality of medical devices based on the priority information of the interfering transmissions.

13. The system of claim 12, wherein the character of the device data is based on an urgency of the device data being transmitted.

14. The system of claim 12, wherein the character of the device data is based on a priority classification structure stored in each medical device.

* * * * *